United States Patent
Smith et al.

(10) Patent No.: US 11,696,855 B2
(45) Date of Patent: *Jul. 11, 2023

(54) BANDAGE

(71) Applicant: BandGrip, Inc., Chicago, IL (US)

(72) Inventors: Fred Smith, Houston, TX (US); Keith Hoglund, Burr Ridge, IL (US); Tom Pruter, Lincolnshire, IL (US)

(73) Assignee: BandGrip, Inc., Chicago, IL (US)

( * ) Notice: Subject to any disclaimer, the term of this patent is extended or adjusted under 35 U.S.C. 154(b) by 352 days.

This patent is subject to a terminal disclaimer.

(21) Appl. No.: 16/888,369

(22) Filed: May 29, 2020

(65) Prior Publication Data
US 2020/0289331 A1    Sep. 17, 2020

Related U.S. Application Data

(63) Continuation of application No. 15/349,484, filed on Nov. 11, 2016, now Pat. No. 10,667,957.

(60) Provisional application No. 62/253,898, filed on Nov. 11, 2015.

(51) Int. Cl.
*A61F 13/00* (2006.01)
*A61B 17/08* (2006.01)
*A61F 13/02* (2006.01)

(52) U.S. Cl.
CPC ........ *A61F 13/0276* (2013.01); *A61B 17/085* (2013.01); *A61F 13/0206* (2013.01); *A61F 13/0226* (2013.01); *A61F 13/0246* (2013.01); *A61F 2013/00119* (2013.01); *A61F 2013/00182* (2013.01)

(58) Field of Classification Search
CPC .................................................. A61B 17/085
See application file for complete search history.

(56) References Cited

U.S. PATENT DOCUMENTS

| | | |
|---|---|---|
| 3,825,010 A | 7/1974 | Mc |
| 4,430,998 A | 2/1984 | Harvey et al. |
| 4,865,026 A | 9/1989 | Barrett |
| 5,603,145 A | 2/1997 | Arakawa |
| 5,968,097 A | 10/1999 | Frechet |
| 6,652,559 B1 | 11/2003 | Tetreault |
| 6,712,830 B2 | 3/2004 | Esplin |
| 7,156,862 B2 | 1/2007 | Jacobs et al. |
| 8,945,156 B2 | 2/2015 | Kubiak et al. |
| 9,414,840 B2 | 8/2016 | Fleischmann |
| 2007/0083140 A1 | 4/2007 | Lohrer |

(Continued)

FOREIGN PATENT DOCUMENTS

| | | |
|---|---|---|
| WO | 9310731 A1 | 6/1993 |
| WO | 2013113906 A1 | 8/2013 |

*Primary Examiner* — Kim M Lewis
(74) *Attorney, Agent, or Firm* — The Watson IP Group, PLC; Jovan N. Jovanovic

(57) ABSTRACT

A bandage comprising a base substrate, a wound covering portion, a first side coupling member and a second side coupling member, and a first side and second side adhesive portion. The base substrate includes a central region, a first side region and a second side region, and comprises an elastic member. The wound covering portion is positioned over the central region. The first side coupling member extends over the first side region. The second side coupling member extending over the second region. The first side adhesive portion is positioned on the first side region. The second side adhesive portion positioned on the second side region. A method of use as well as a protective carrier are likewise disclosed.

9 Claims, 5 Drawing Sheets

(56) References Cited

U.S. PATENT DOCUMENTS

2011/0257571 A1   10/2011  Fritsch
2015/0305739 A1   10/2015  Rolandi et al.
2017/0333039 A1    3/2017  Leung
2017/0231826 A1    8/2017  Smith

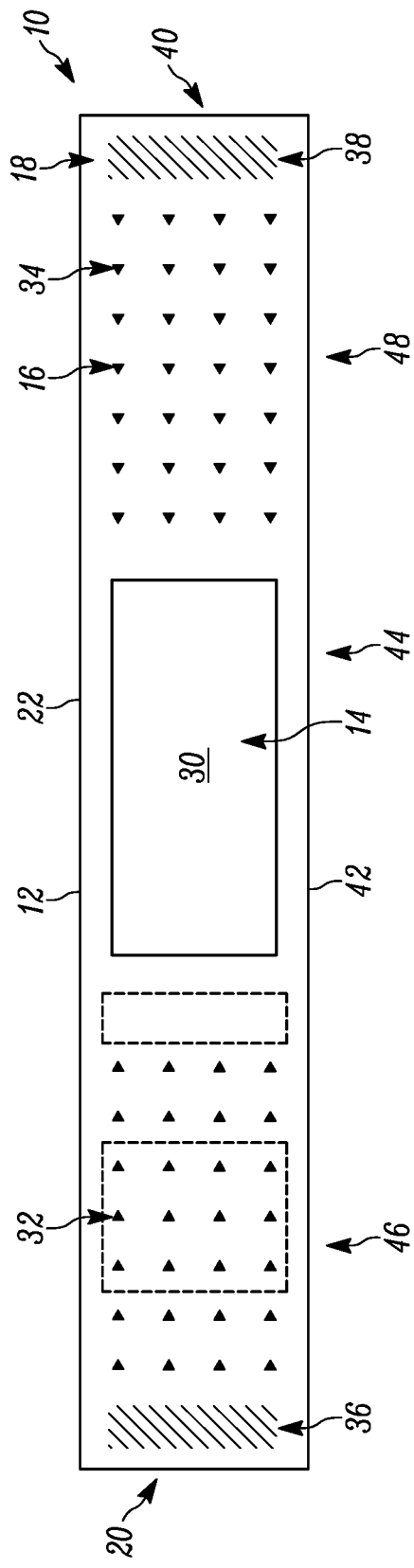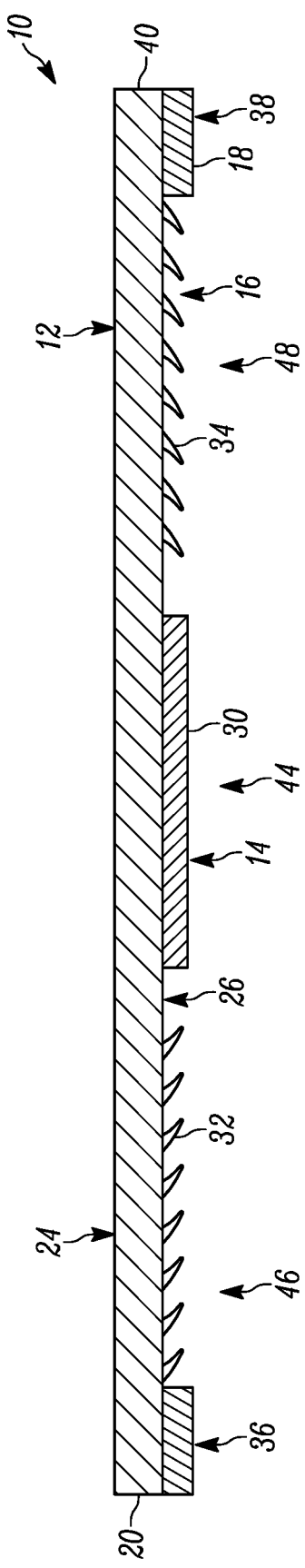

BANDAGE

CROSS-REFERENCE TO RELATED APPLICATION

This application is a continuation of U.S. patent application Ser. No. 15/349,484 filed Nov. 11, 2016, entitled "Bandage", which claims priority from U.S. Pat. App. Ser. No. 62/253,898 filed Nov. 11, 2015, entitled "Bandage", the entire specification of which is hereby incorporated by reference in its entirety.

BACKGROUND OF THE DISCLOSURE

1. Field of the Disclosure

The disclosure relates in general to wound treatment devices, and more particularly, to a bandage which both provides a cover over a wound and also aids in the closure of a wound.

2. Background Art

The use of bandages is well known in the art. Generally, bandages include a covering material and a base substrate. The covering material is coupled to the base substrate and the base substrate is adhered to the skin of a user.

Often, a wound that is deep may require stitches or the like to provide the necessary closure. Problematically, a typical bandage while helpful, often does not provide any, or sufficient force on a wound to direct the opposing sides of the wound to meet or to otherwise foster closure.

It would be advantageous for a bandage that could provide covering for a wound as well as forces to facilitate, foster and/or urge wound closure.

SUMMARY OF THE DISCLOSURE

In an aspect of the disclosure, the disclosure is directed to a bandage comprising a base substrate, a wound covering portion, a first side coupling member and a second side coupling member, and a first side and second side adhesive portion. The base substrate comprises an elastic member and includes a central region, a first side region and a second side region. The wound covering portion is positioned over the central region. The first side coupling member extends over the first side region. The second side coupling member extending over the second region. The first side adhesive portion is positioned on the first side region. The second side adhesive portion positioned on the second side region.

It is contemplated that, in operation, the user would take the first side region and couple the same on one side of wound. Then, the user would stretch the material and couple the second side region on the other side of the wound. The wound may be pinched at the same time. Once both are coupled, the first and second side coupling members (micro needles) are directed into the skin of the user, and due to configuration, generally preclude inward movement of the base substrate relative to the skin toward the wound. The adhesive portions, maintain the position of the bandage and foster the engagement and mechanical locking of the coupling members and the skin on either side of the wound. The biasing force of the base substrate provides the necessary closure force to direct opposing sides of the wound toward each other to close the wound.

In some configurations, the first side coupling member is positioned between the central region and the first side adhesive portion and wherein the second side coupling member is positioned between the central region and the second side adhesive portion.

In some configurations, the wound covering portion further includes a gauze positioned thereon.

In some configurations, the base substrate is one of transparent and opaque.

In some configurations, at least one of the first side coupling member and the second side coupling member further comprises a base and a plurality of gripping structures. The base has a lower surface and an upper surface, and defines an outer perimeter. The outer perimeter has a leading edge and a trailing edge. The plurality of gripping structures extend outwardly from the base, and are spaced apart from each other. Each of the gripping structures is curved toward the leading edge.

In some configurations, the gripping structures each include a leading surface and a trailing surface, and opposing first side surface and second side surface, together defining a base perimeter at the base and an upper tip distally therefrom. The opposing first side surface and second side surface are inwardly angled to meet at the upper tip. The leading surface and the trailing surfaces are curved toward the leading edge. The upper tip lies outside of a footprint defined by the base perimeter.

In some configurations, the base perimeter comprises a square.

In some configurations, the gripping structures are positioned in rows between opposing side edges, with the gripping structures of adjacent rows being staggered.

In some configurations, the gripping structures are positioned in two rows wherein the gripping structures of a first row are staggered relative to the gripping structure of a second row.

In some configurations, the gripping structures are substantially identical.

In some configurations, the first side coupling member comprises a monolithic formed acrylic polymer member.

In some configurations, the first side coupling member and the second side coupling member are substantial mirror images of each other.

In another aspect of the disclosure, the disclosure is directed to a method of treating a wound. The method comprises the steps of providing a bandage of claim 1 in an unstretched configuration; placing the first side coupling member onto a first side of the wound; adhering the first side adhesive portion to the first side of the wound; stretching the base substrate of the bandage; placing the second side coupling member one a second side of the wound, while maintaining the base substrate of the bandage stretched; adhering the second side adhesive portion to the second side of the wound; and releasing the base substrate so that the bandage returns toward the unstretched configuration, and in turn, closes the wound.

In some configurations, the method includes the step of adhering the second side adhesive portion to the second side of the wound is completed while maintaining the base substrate of the bandage stretched.

In some configurations, the base substrate comprises a transparent material. The method further comprises the step of: monitoring the wound through the base substrate.

In another aspect of the disclosure, the disclosure is directed to a combination protective carrier and mechanical coupling system for utilization in association with manufacturing of a bandage. The protective carrier comprises a base with opposing first sidewall and second sidewall, cooperatively defining a channel. The protective carrier being elongated and structurally configured to be rolled onto itself. The mechanical coupling system comprises a base having a plurality of gripping structures extending therefrom, wherein the gripping structures remain within the channel defined by the protective carrier. The mechanical coupling system is positioned within the protective carrier, and rolled onto itself.

In some configurations, the gripping structures are curved toward a first a side of the mechanical coupling system.

BRIEF DESCRIPTION OF THE DRAWINGS

The disclosure will now be described with reference to the drawings wherein:

FIG. 1 of the drawings is a schematic bottom plan view of the bandage of the present disclosure, showing, in particular, mechanical coupling system that is out of scale, but for pictorial clarity; and FIG. 2 of the drawings is a schematic side elevational view of the bandage of the present disclosure;

DETAILED DESCRIPTION OF THE DISCLOSURE

Figure 3:
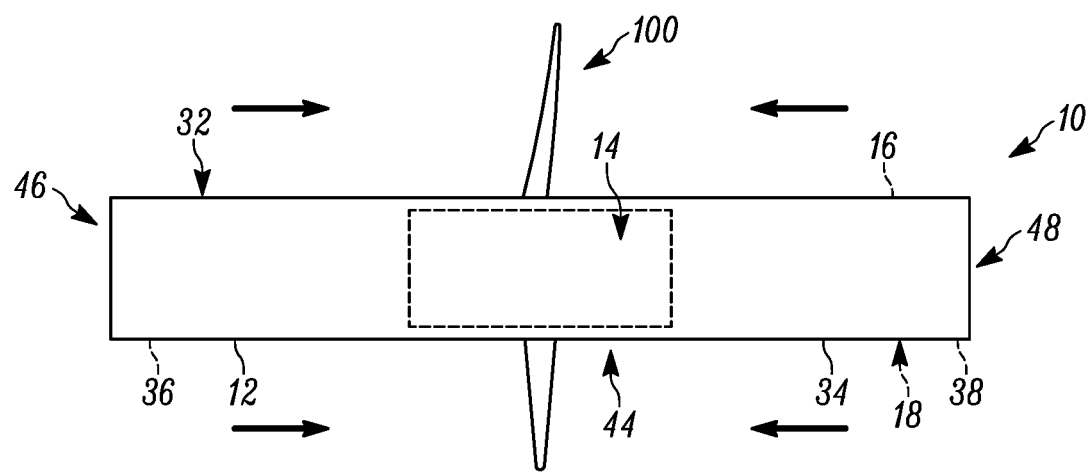
FIG. 3 of the drawings is a top plan view of the bandage placed over a wound.

While this invention is susceptible of embodiment in many different forms, there is shown in the drawings and described herein in detail a specific embodiment with the understanding that the present disclosure is to be considered as an exemplification and is not intended to be limited to the embodiment illustrated.

It will be understood that like or analogous elements and/or components, referred to herein, may be identified throughout the drawings by like reference characters. In addition, it will be understood that the drawings are merely schematic representations of the invention, and some of the components may have been distorted from actual scale for purposes of pictorial clarity.

Referring now to the drawings and in particular to FIG. 1, the bandage of the present disclosure is shown generally at 10. The bandage includes base substrate 12, wound covering portion 14, mechanical coupling system 16 and adhesive coupling system 18. It is contemplated that the bandage of the present disclosure is well suited for wound closure and protection. It will further be understood that the present disclosure is further well suited for other purposes, and the disclosure is not limited to any particular use or application.

The base substrate 12 is shown in FIGS. 1 and 2 as extending between first end 20 and second end 40 and spanning between first side edge 22 and second side edge 42.

The base substrate includes an outer surface 24 which faces outwardly when applied to the skin of a user, and an inner surface 26 that abuttingly overlies the skin of the user. The base substrate 12 includes central region 44, with first side region 46 extending from a first side of the central region and a second side region 48 extending from a second side of the central region opposite the first side region 46.

It is contemplated that the base substrate is substantially uniform in thickness. In the configuration shown, the width is likewise substantially uniform, and the base substrate is substantially symmetrical about both an axis that bisects the base substrate along a longitudinal axis between the first end and the second end, as well as symmetrical about a transverse axis between the first side edge and the second side edge. It is contemplated that in other configurations, the base substrate may or may not be symmetrical and may or may not be uniform. A number of different configurations are contemplated, and the disclosure is not limited to any particular shape of the base substrate.

It is envisioned that the base substrate is elastic and may comprise a woven or non woven natural or synthetic material. Such a material, preferably has some level of elastic stretching at least in a longitudinal direction such that the first end and the second end can be pulled relative to each other to elastically elongate the bandage. In other configurations, the substrate may be elastically deformable in any number of different directions. It is also contemplated that non-synthetic materials are contemplated for use, and that such materials may be woven or non-woven. It is further contemplated that while the material of the base substrate is shown to be uniform, variations are contemplated wherein the base substrate may comprise a number of different materials that are coupled together to form the base substrate.

The wound covering portion 14 is shown as comprising some type of gauze material with an absorbent material positioned therein. The wound covering portion typically comprises a material that is adhered to the inner surface 26 of the base substrate, and includes wound contact surface 30. It is contemplated that the wound covering portion 14 may include absorbent material, medicament, among other features. That is, such features are known to those of ordinary skill in the bandage arts.

The mechanical coupling system 16 is shown in FIGS. 1 and 2 as comprising first side coupling member 32 and second side coupling member 34. The first and second side coupling members are contemplated to be substantially identical (although property, size, quantity and the like may be varied, the generally have the same operational characteristics). It will be understood that they may be different, while still having the same functionality. As such, the first side coupling member 32 will be described with the understanding that the second side coupling member 34 may be selected from the same materials and configurations.

The first side coupling member 32 comprises an array of 700 micron micro needles that can be bloodlessly and painlessly be directed into the dermis of the user. The micro needles extend from a substantially planar base surface, and may be formed from a starting material that is substantially planar. The base surface is adhered to the inner surface 26 of the base substrate. In other configurations it is contemplated that the base surface of the micro needles may form a portion of the base substrate. In other configurations, the micro needles may comprise structures shown in PCT Published Application entitled "Microstructure-Based Wound Closure Devices", Publication No. WO 2013/188884A1, by Applicant University of Washington Through Its Center for Commercialization, the entire specification of which is hereby incorporated by reference in its entirety. Certain other configurations are likewise contemplated for use. It will further be understood that the micro needle may be straight, slanted or hooked, among other configurations. In the configuration shown, the micro needles are slanted inwardly toward the central region, while other configurations are contemplated.

It is contemplated that the first side coupling member span across the entirety of the base substrate from first side edge to second side edge. In the configuration shown, the first side coupling member is positioned so as to be spaced apart from both the wound covering portion and the respective end of the base substrate. In other configurations, the first side coupling member and the second side coupling member may comprise discrete regions rather than a substantially continuous member as is shown in the configuration.

Figure 4:
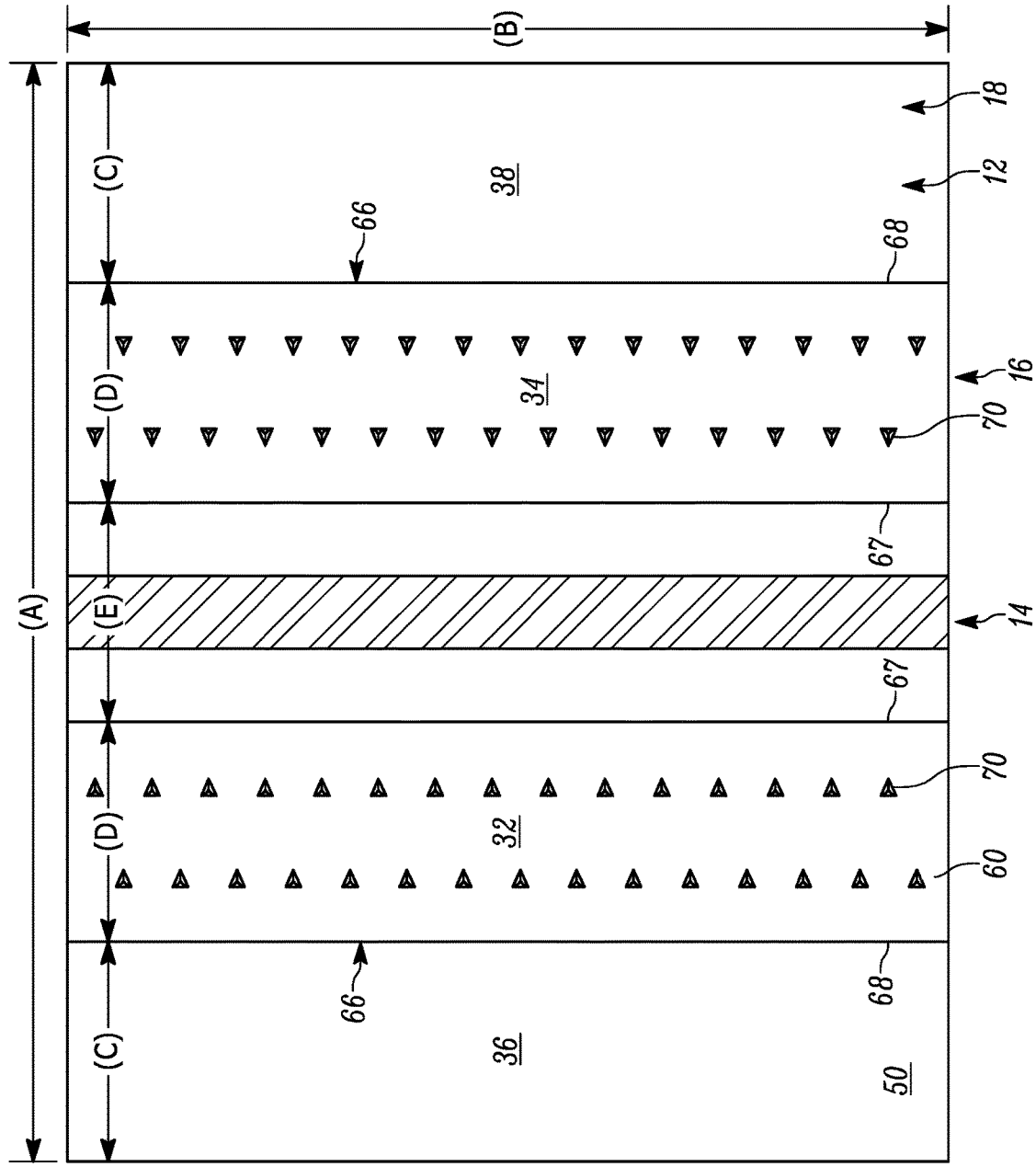
FIG. 4 of the drawings is a bottom plan view of another configuration of the bandage of the present disclosure, showing, in particular, the dimensions of the configuration.
Figure 5:
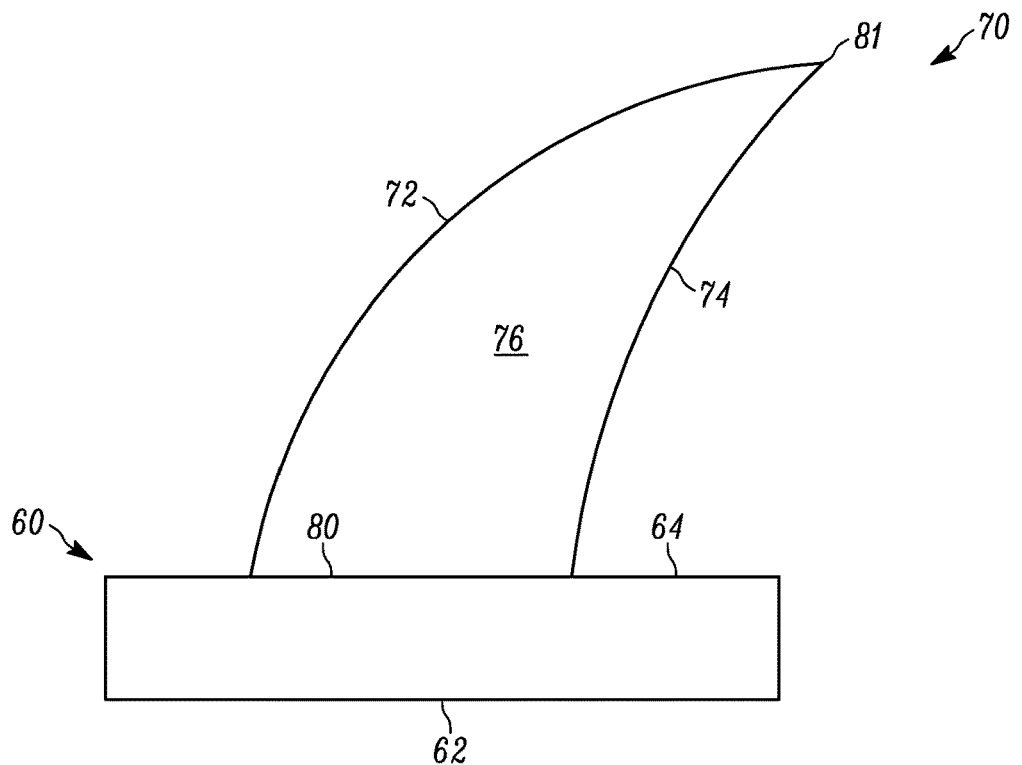
FIG. 5 of the drawings is a partial side elevational view of the first side coupling member, showing, in particular, the configuration of the gripping structure.
Figure 6:
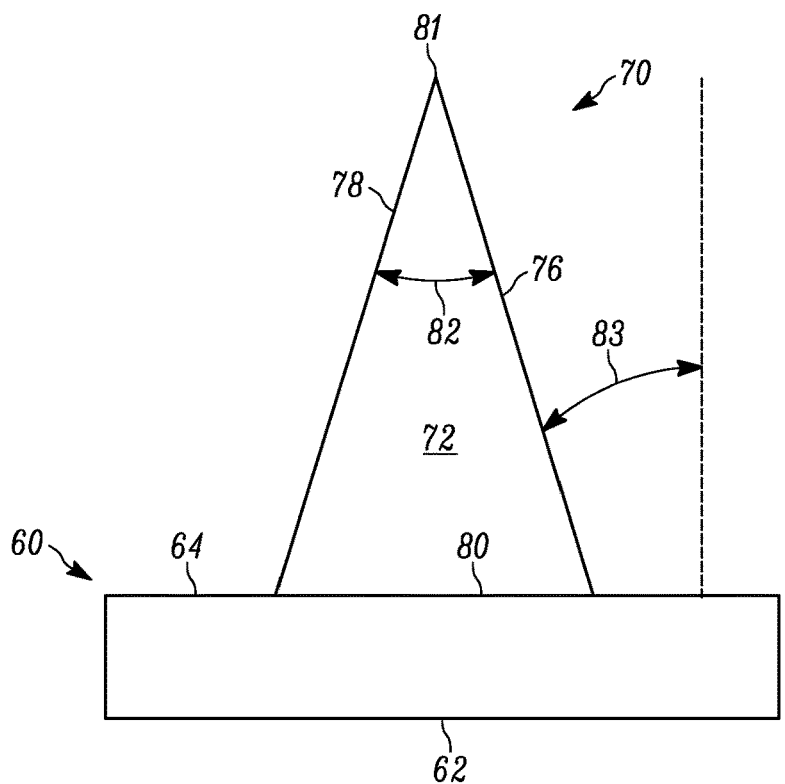
FIG. 6 of the drawings is a partial back elevational view of the first side coupling member, showing, in particular, the configuration of the gripping structure.

More particularly, the first side and second side coupling members may be mirror images of each other, and may comprise the structure shown in FIGS. 4 through 6, collectively. In particular, the coupling members may each comprise a base 60 and a plurality of spaced apart gripping structures 70. The base generally comprises a substantially planar member defining a lower surface 62, an upper surface 64 and outer perimeter 66. In the configuration shown, the base has a thickness of 0.25 millimeters. When mounted in the operable configuration, the outer perimeter 66 defines a leading edge 67 and a trailing edge 68. In the configuration shown, the base comprises a substantially uniform rectangular member with the longer sides thereof being the leading and trailing edges, which are parallel to each other. Of course, other configurations are contemplated, including structures that have additional topographies.

The gripping structures 70 are spaced about the base 60 and extend from the upper surface 64 thereof. It will be understood that such structures are monolithic and conformed along with the base to form a single substantially uniform configuration. The gripping structures are generally (although not required to be) substantially identical in configuration. As such, a single gripping structure is shown with the understanding that the remaining gripping structures are substantially identical.

Figure 7:
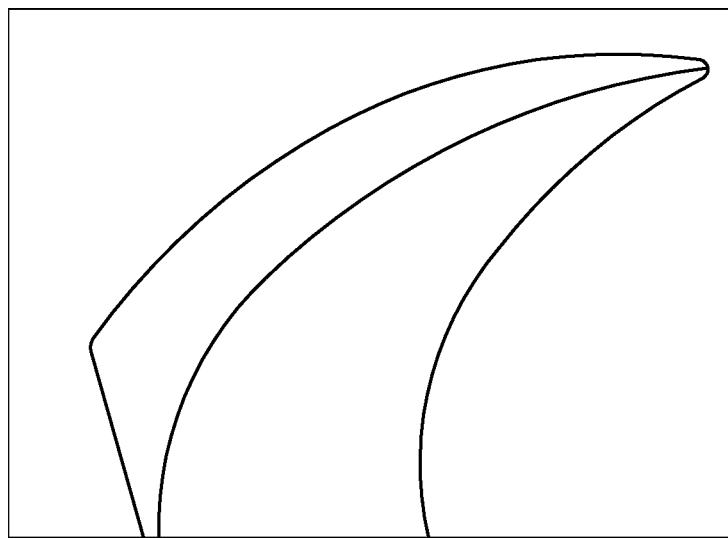
FIG. 7 of the drawings is a photograph showing a perspective view of a gripping structure of the present disclosure.

The gripping structure 70 includes leading surface 72, trailing surface 74, first side surface 76 and second side surface 78. The gripping structure at the base defines a base perimeter 80, which is substantially square. The four surfaces 72, 74, 76 and 78 cooperatively taper to an upper tip 81. The outer surfaces are angled inwardly at angle 83 which, in the configuration shown is 12.02° with the included angle 82 of 24.04°. In the configuration shown, the height of the gripping structures is 0.700 mm. with a base that is 0.426 mm square. The leading and trailing surfaces are each curved so that the tip lies outside of the footprint defined by the base perimeter, with the first and second side surfaces being inclined at the angles identified above. Of course, variations are contemplated. It has been found that the curved surfaces of the leading and trailing surfaces greatly aids in the retention strength of the gripping structures as compared to straight or angled gripping structures. A magnification photograph of a gripping structure is shown in FIG. 7.

In the configuration shown, the gripping structures are positioned in uniform rows an columns, which are offset relative to each other. In such a configuration, a total of 15 gripping structures may be positioned in each of two rows, with the rows being staggered so that the gripping structures of one row fall between adjacent gripping structures of the second row. Of course, variations are contemplated, for example, a configuration wherein the structures are in uniform rows and columns forming a grid-like structure with uniform separation in either direction. In the configuration shown, the material from which the first and second side coupling members are formed comprise an acrylic polymer material formed from an acrylic polymer resin. The formation is not limited to use in association with the disclosed polymer constructions, and other polymer constructions are contemplated for use.

The adhesive coupling system 18 is shown in FIG. 1 as comprising first side adhesive portion 36 and second side adhesive portion 38. It will be understood that the first and second side adhesive portions may generally be similar in construction. Thus, while they may be placed in identical locations or in different locations, these general adhesive construction is similar. As such, first side adhesive portion 36 will be discussed with the understanding that the same principles and constructions may be applied to second side adhesive portion 38.

The first side adhesive portion 36 may comprise a plurality of regions, or a single region of adhesive that can be releasably stuck to the skin of the patient with proper adhesion to facilitate retention thereof. Most preferably, the first side adhesive portion 36 includes one or more regions, all of which regions are positioned between the first side coupling member 32 and the first end 20 of the base substrate. It is contemplated that the same construction is utilized on the second side adhesive portion 38 such that it is between the second side coupling member 34 and the second end 40 of the base substrate 12. The adhesive is of the type know to those of skill in the bandage art. That is, such adhesive is configured to adhere to the skin of the user with sufficient force. It is contemplated, in other configurations, that multiple regions of adhesive be utilized for both the first side adhesive portion and the second side adhesive portion, and that such regions may be positioned over the mechanical coupling system, between the mechanical coupling system and the respective ends, or between the mechanical coupling system and the wound covering system, or in all three locations. It has been found that most preferably, the region of choice is between the mechanical coupling system and the respective end of the base substrate. It is contemplated that the adhesive may extend over the entirety of the inner surface 26 of the base substrate so that the wound covering portion and the mechanical coupling system is coupled to the base substrate with the same adhesive which forms the first and second side adhesive portions.

In the configuration shown in FIG. 4 through 6, the dimensions of a sample bandage formed by the present disclosure is shown. The dimensions are exemplary, and not to be deemed limiting. The length of the bandage (A) is 63.50 mm. The width of the bandage (B) is 50.80 mm. The length of each of the first and second side adhesive portions (C) is 12.70 mm. The length of each of the first and second side coupling members (D) is 12.70 mm. The length of the space between the first and second side coupling members, i.e., the wound contact surfaced (E) is 12.70 mm. Again, these are merely exemplary. It is contemplated that some of the bandages may have half of the width.

In operation, the bandage is first provided. In the preferred configuration, the base substrate 12 includes a wound covering portion 14 generally centrally located, with a first side coupling member on the first side region and a second side coupling member flanking on the second side region. A first side adhesive portion extends between the first side coupling member and the first end with a second side adhesive portion extending between the second side coupling member and the second end. Of course, other configurations are likewise contemplated, and are described above.

To apply the bandage, generally, and conceptually, with reference to FIG. 3, the bandage is stretched so as to provide an inward biasing force, with the adhesive providing the additional mechanical retention on either side of the wound 100.

In more detail, with a typical wound of the type contemplated to be treated by the present bandage, which is a wound that is a cut through layers of the skin along an elongated path, with the path having a first end and a second end, and skin on either side thereof. With such a wound, or other similar wounds, the user (or the medical professional) would first adhere the first side adhesive portion and the first side coupling member to the skin on a first side of the wound. That is, the coupling would be to skin on the first side of the wound. It will be understood that the first side coupling member, and the micro needles extend into the upper layers of the skin, preferably without pain and without severing any capillaries to cause visible blood flow. As the hooks are configured to extend toward the wound, the hooks serve to prevent further movement of the entire substrate toward the wound. Additionally, the adhesive is applied to the skin so as to further facilitate the direction of the micro needles into the skin and to preclude skipping or movement along the skin. That is, the adhesive insures that the micro needles will operatively extend into the skin and remain in the proper orientation. Generally, this occurs in the unstretched configuration.

Next, the user (or medical professional) stretches the base substrate so as to extend on the other side of the wound. The second side region is then directed into the skin. In turn, the second side coupling member is directed into the skin forcing the micro needles into the skin. As these micro needles are likewise angled toward the wound, further movement of the substrate toward the wound is limited and precluded. The second side adhesive portion is then pressed onto the skin to secure the second side region to the skin, and to maintain the micro needles in the proper orientation.

In such a configuration, the wound covering portion 14 extends over the wound, and, preferably, the wound contact surface 30 contacts the surface of the wound. The wound contact surface may provide for pressure on the wound to facilitate clotting, or may provide medicament which may otherwise be beneficial.

Due to the elasticity of the base substrate and to the elastic stretching of the base substrate over the wound prior to the attachment of the second side region to the skin, when coupled the base substrate will exert a biasing force to return to its original configuration. As the base substrate attempts to return to its original unstretched configuration, the micro needles resist such movement with the adhesive both precluding such movement and also precluding the retraction of the micro needles from the skin. As such, the micro needles that extend into the skin on either side of the wound force the skin toward the wound so that the biasing force exerted by the base substrate forces the wound closed, and a general pinching of the skin. Such an operation fosters wound closure, blood clotting, and minimization of scarring. Further, the same is achieved without increasing the pain or without causing further damage to the skin around the wound.

Figure 8:
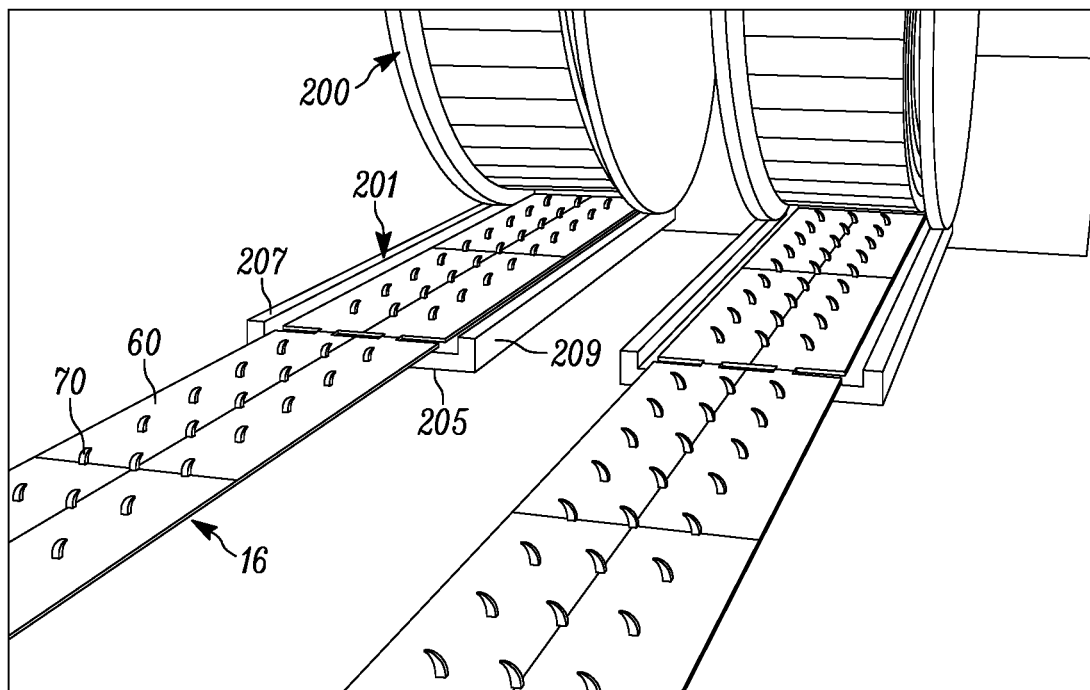
FIG. 8 of the drawings is a perspective view of the protective carrier within which a roll of the mechanical coupling system can be positioned for assembly and manufacturing purposes.

To manufacture a bandage of the present configuration, it is contemplated that the base substrate, the wound covering portion and the mechanical coupling systems may be provided on rolls with the components being joined together. Problematically, it may be difficult to provide a roll of the mechanical coupling system without damaging the gripping structures. In such configurations, the mechanical coupling system is provided on a roll encased, at least partially by a protective encasement. For example, a roll of what would become the mechanical coupling system is provided, wherein one side forms the leading edge of the coupling member, and the other side forms the trailing edge of the coupling member, can be placed within a channel 201 of a protective carrier 200, shown in FIG. 8. The protective carrier channel 201 is defined by a base 205, first sidewall 207 and second sidewall 209. The protective carrier 200 has a length that is commensurate with the length of the roll of the mechanical coupling system material. The roll of the mechanical coupling system is placed within the channel, with the gripping structures facing in an upward direction. It will be understood that the height of the first and second sidewalls 207, 209 is such that the gripping structures are maintained within the channel 201 defined thereby. During manufacturing, the mechanical coupling system material can be removed from within the channel 201 at the time of application thereof onto the base substrate, and the adhesive positioned thereon. In the configuration shown, two side by side rolls of mechanical coupling system material housed within respective protective carriers can be utilized and can be coupled together to form a cartridge, for example, wherein mechanical coupling system material can be removed from each to substantially simultaneously form the first side coupling member and the second side coupling member. It is contemplated that the roll may be rolled upon itself, and that the roll may comprise between 5 and 100 feet of mechanical coupling system that can be utilized to form the bandage.

The foregoing description merely explains and illustrates the invention and the invention is not limited thereto except insofar as the appended claims are so limited, as those skilled in the art who have the disclosure before them will be able to make modifications without departing from the scope of the invention.

What is claimed is:

1. A bandage comprising:
   a base substrate having a central region, a first side region and a second side region, at least the central region comprising an elastic material;
   a first side coupling member that is rigid and integrally molded, the first side coupling member attached to the first side region of the base substrate and a second side coupling member that is rigid and integrally molded, the second side coupling member attached to the second side region of the base substrate, each of the first side coupling member and the second side coupling member including:
      a base having a lower surface and an upper surface, and defining a outer perimeter having a leading edge, with the lower surface attached to the respective one of the first side region of the base and the second side region of the base; and
      a plurality of gripping structures integrally molded with extending outwardly from the base, and spaced apart from each other, each of the gripping structures being curved toward the leading edge, wherein the gripping structures each include a leading surface and a trailing surface, and opposing first side surface and second side surface, together defining a base perimeter at the base and an upper tip distally therefrom, with the leading surface being substantially parallel to the leading edge of the base, the opposing first side surface and second side surface inwardly angled to meet at the upper tip, with the leading surface and the trailing surfaces being curved toward the leading edge each at a different radius of curvature, wherein the upper tip lies outside of a footprint defined by the base perimeter.

2. The bandage of claim 1 wherein the plurality of gripping structures of each of the first side coupling member and the second side coupling member are arranged in a plurality of rows, with the rows being substantially parallel with the leading edge.

3. The bandage of claim 2 wherein the gripping structures of each of the first side coupling member and the second side coupling member are staggered relative to an adjacent row.

4. The bandage of claim 1 further comprising a first side adhesive portion positioned on the first side region of the base substrate and a second side adhesive portion positioned on the second side region of the base substrate.

5. The bandage of claim 4 wherein the first side coupling member is positioned between the central region and the first side adhesive portion, and wherein the second side coupling member is positioned between the central region and the second side adhesive portion.

6. The bandage of claim 1 further comprising a wound covering portion positioned over the central region.

7. The bandage of claim 6 wherein the wound covering portion comprises gauze.

8. The bandage of claim 1 wherein the first side coupling member and the second side coupling member are mirror images of each other.

9. The bandage of claim 1 wherein the entirety of the base substrate comprises an elastic material.

* * * * *